United States Patent
Kwon et al.

(10) Patent No.: US 8,512,720 B2
(45) Date of Patent: Aug. 20, 2013

(54) COSMETIC COMPOSITION FOR MASSAGE

(75) Inventors: Lee Kyoung Kwon, Yongin-si (KR); Mi Hyun Oh, Seoul (KR); Jeong Cheol Ha, Yongin-si (KR); Jun Oh Kim, Yongin-si (KR); Yeon Joon Kim, Seoul (KR); Sang Hoon Han, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 13/498,674

(22) PCT Filed: Sep. 29, 2010

(86) PCT No.: PCT/KR2010/006606
§ 371 (c)(1),
(2), (4) Date: Mar. 28, 2012

(87) PCT Pub. No.: WO2011/040747
PCT Pub. Date: Apr. 7, 2011

(65) Prior Publication Data
US 2012/0184629 A1    Jul. 19, 2012

(30) Foreign Application Priority Data
Sep. 30, 2009    (KR) .................. 10-2009-0092975

(51) Int. Cl.
*A61K 8/06*    (2006.01)
(52) U.S. Cl.
USPC ............................. 424/401; 424/63; 514/54

(58) Field of Classification Search
None
See application file for complete search history.

(56) References Cited

U.S. PATENT DOCUMENTS
2011/0002865 A1 *    1/2011    Fournial et al. .............. 424/70.1

FOREIGN PATENT DOCUMENTS
| CN | 101732188 | * 11/2008 |
| EP | 1 920 762 | 5/2008 |
| JP | 2007-238516 | 9/2007 |

OTHER PUBLICATIONS
International Search Report for PCT/KR2010/006606, mailed Jun. 1, 2011.

* cited by examiner

*Primary Examiner* — Janet Epps-Smith
*Assistant Examiner* — Yanzhi Zhang
(74) *Attorney, Agent, or Firm* — Nixon & Vanderhye P.C.

(57) ABSTRACT

The present invention relates to a cosmetic composition for massage, and more particularly, to a cosmetic composition for massage that provides a smooth rolling sensation even with a low oil content by controlling the ratio and content of polar and nonpolar oils and properly penetrates into the skin according to the control of the absorption rate by using a gum, which solves the problems with the existing massage compositions such as greasiness caused by a high content of oily ingredients and inconvenience associated with a need for cleansing the skin after use.

6 Claims, 2 Drawing Sheets

COSMETIC COMPOSITION FOR MASSAGE

This application is the U.S. national phase of International Application No. PCT/KR2010/006606 filed 29 Sep. 2010 which designated the U.S. and claims priority to KR 10-2009-0092975 filed 30 Sep. 2009, the entire contents of each of which are hereby incorporated by reference.

TECHNICAL FIELD

The present invention relates to a cosmetic composition for massage, and more particularly, to a cosmetic composition for massage that provides a smooth rolling sensation even with a low oil content by controlling the ratio and content of polar and nonpolar oils and properly penetrates into the skin according to the control of the absorption rate by using a gum, which solves the problems with the existing massage compositions such as greasiness caused by a high content of oily ingredients and inconvenience associated with a need for cleansing the skin after use.

BACKGROUND ART

The conventional cosmetic products for skin massage include water-based gel formulations containing a large quantity of water-soluble polymers to impart a cool feeling to the skin, oil-based formulations containing oily ingredients thickened with an oil thickener to help cleansing makeup, and cream type formulations containing a high content of oil greater than 35 wt. % so that it can be used for massage through oil phase inversion and then wiped off or washed out with water.

A water-based massage gel provides a cool feeling to the skin due to high water content and a massage effect using the glide of polymers, consequently with a poor massage control relative to the oil-based formulations. The oil-based type is well spreadable on the skin to maximize stimulation of blood circulation and removal of makeup, but with a high oil content, it has a poor high-temperature stability that causes many limitations in its applications and provides an unpleasant feeling on the skin greasy during or after use and an inconvenience associated with a need for cleansing the skin. The most popular massage creams contain a large quantity of oil, about 30 to 50 wt. %, which provides a good massage feeling but poor formulation stability, causing a great change of properties pertaining to a change of temperature during the process, and leaves the skin greasy after use, requiring the user to wipe the excess cream with tissue paper and then rinse off with water.

The conventional massage formulations with high oil content provide a good massage control with an uncomfortable massage feeling and an inconvenience of cleansing the skin due to greasiness, but those with low oil content provide a cool feeling with a poor massage control. Many technical solutions have been suggested persistently to such problems with the conventional massage formulations.

DISCLOSURE OF INVENTION

Technical Problem

Accordingly, the inventors of the present invention have found out that a cosmetic composition for massage comprising 1 to 5 wt. % of a saccharide surfactant, 5 to 25 wt. % of an oil, with a mixing ratio of a polar oil to a nonpolar oil being 1~3:1, and 0.1 to 3 wt. % of a gum provides an enhanced rolling sensation and hence a smooth massage control even with a low oil content relative to the conventional massage formulations by controlling the ratio and content of polar and nonpolar oils, avoids greasy skin caused by high oil content, and easily penetrates into the skin by control of the composition absorption rate pertaining to the use of a gum, thereby eliminating an inconvenience of cleansing the skin after use.

It is therefore an object of the present invention to provide a composition that secures a good massage control even with a low oil content to avoid the greasy skin and easily penetrates into the skin by control of the absorption rate due to the use of a gum, thereby eliminating an inconvenience of cleansing the skin.

Technical Solution

To accomplish the above object, according to the present invention, there is provided a cosmetic composition for massage that includes, with respect to the total weight of the composition, 1 to 5 wt. % of a saccharide surfactant, 5 to 25 wt. % of an oil, and 0.1 to 3 wt. % of a gum, the oil being composed of polar and nonpolar oils at a ratio of 1~3:1.

Advantageous Effects

The cosmetic composition for massage according to the present invention can enhance the rolling sensation to provide a smooth massage control even with a low oil content relative to the conventional massage formulations by controlling the ratio and content of polar and nonpolar oils, and avoid the greasy skin caused by high oil content, and easily penetrates into skin by control of the absorption rate due to the use of a gum, thereby eliminating inconvenience associated with a need for cleansing the skin after use. Compared with the conventional cosmetic formulations for massage, the present invention can make a difference in massage effect and comfortable massage feeling.

BEST MODE FOR CARRYING OUT THE INVENTION

Figure 1:
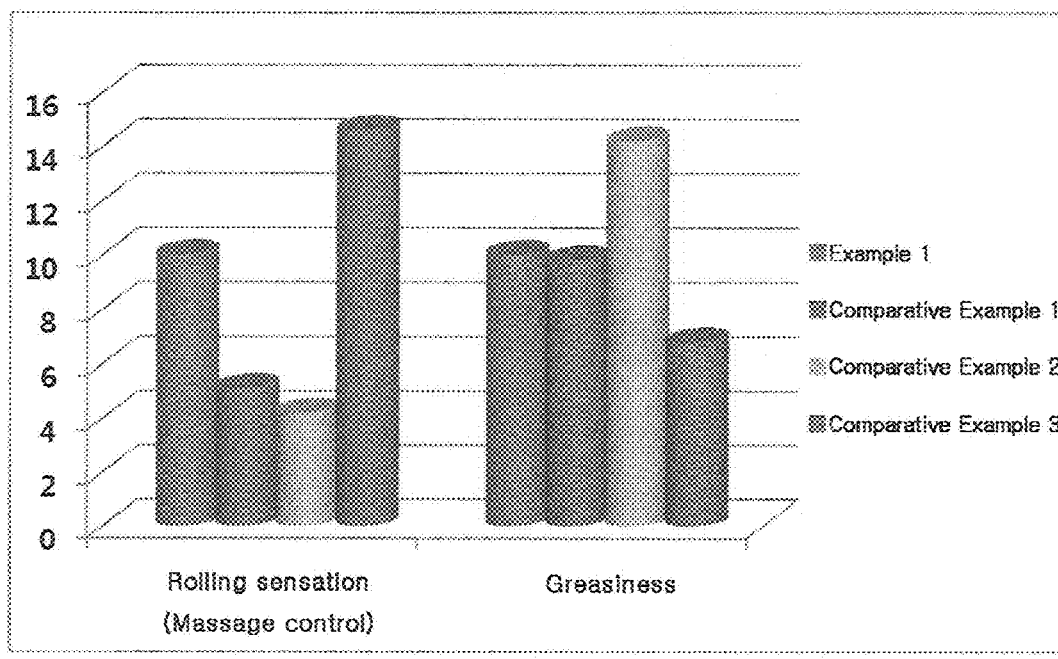
FIG. 1 shows the results of a sensory evaluation in regard to massage control and greasiness as conducted on the compositions of Example 1 and Comparative Examples 1, 2 and 3.

The cosmetic composition for massage according to the present invention, which provides a non-greasy massage control with controlled absorption rate and easily penetrates into skin with no inconvenience of cleansing the skin after use, includes: with respect to the total weight of the composition, 1 to 5 wt. % of a saccharide surfactant; 5 to 25 wt. % of an oil, the oil including a polar oil and a nonpolar oil at a ratio of 1~3:1; and 0.1 to 3 wt. % of a gum.

The saccharide surfactant as used herein refers to a saccharide surfactant prepared from a saccharide by an esterification reaction with an alkyl fatty acid, or by an etherfication reaction with a higher alcohol. The saccharide as used herein refers to a polyol having at least one alcohol functional group (—OH), with/without an aldehyde or ketone functional group, and containing at least 4 carbon atoms, preferably 5 to 6 carbon atoms. The polyol may be cyclized or non-cyclized monosaccharides-polyhydroxyaldehyde (i.e., aldose) or polyhydroxyketone (i.e., ketose). The specific examples of the aldose may include ribose, xylose, arabinose, glucose (given by the formula 1), mannose, or galactose. The specific examples of the ketose may include xylulose or fructose (given by the formula 2). The saccharide surfactant may include at least one of these monosaccharides combined with alkyl fatty acid or higher alcohol.

The present invention contains 1 to 5 wt. % of the saccharide surfactant with respect to the total weight of the composition. The saccharide surfactant, when emulsified with the same amount of oil, provides an enhanced massage control relative to other PEG-based surfactants. The content of the saccharide surfactant less than 1 wt. % results in incomplete emulsification, with a failure to acquire formulation stability. The content of the saccharide surfactant exceeding 5 wt. % renders the composition thickened too much to provide a smooth massage control. Hence, the preferred content of the saccharide surfactant is in the range of 1 to 5 wt. %.

The oil as used in the composition of the present invention may include the polar and nonpolar oils at a mixing ratio of 1~3:1 in an amount of 5 to 25 wt. % with respect to the total weight of the composition. The ratio of polar to nonpolar oils less than 1:1, where the proportion of the polar oil is less than 1, deteriorates the rolling sensation that is a great benefit from the polar oil, and increases greasiness from the nonpolar oil. The proportion of the polar oil exceeding 3 greatly enhances the rolling sensation with reduced greasiness, but a large content of the polar oil makes the surface of the formulation unstable, with a deterioration of the formulation stability. The oil content less than 5 wt. % results in a failure to provide an oil-based smooth massage control, while the oil content exceeding 25 wt. % results in an absolutely large quantity of oil, which makes the composition too greasy to penetrate into skin, consequently with an unstable massage formulation.

[Formula 1]

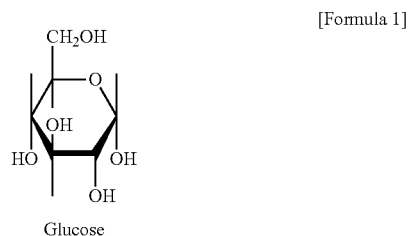

Glucose

[Formula 3]

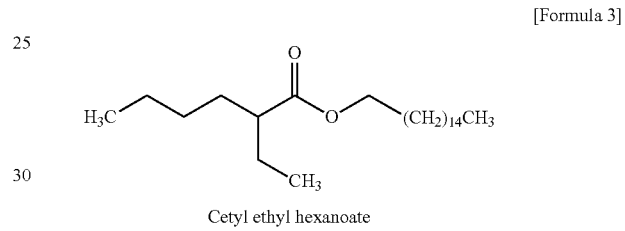

Cetyl ethyl hexanoate

[Formula 2]

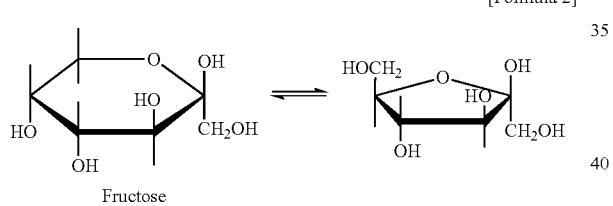

Fructose

[Formula 4]

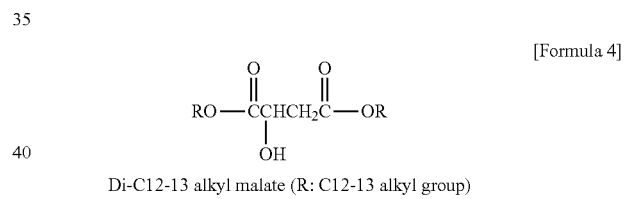

Di-C12-13 alkyl malate (R: C12-13 alkyl group)

[Formula 5]

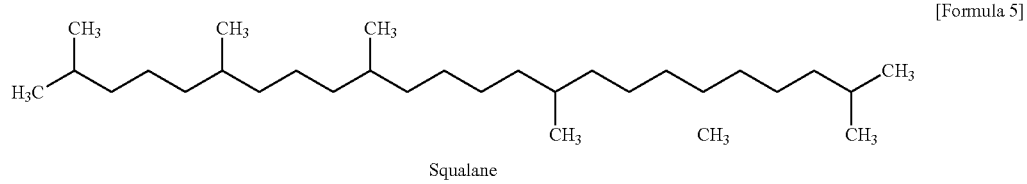

Squalane

The polar oil as used herein refers to oils containing at least one functional group selected from carboxyl group (COO—), ketone group (CO—), or hydroxyl group (—OH) and may include at least one of those oils. The specific examples of the polar oil may include cetyl ethyl hexanoate (given by the formula 3), di-C12-13 alkyl malate (given by the formula 4), etc.

The nonpolar oil as used herein refers to hydrocarbon oils consisting of hydrocarbon alone and may include at least one of those hydrocarbon oils. The specific examples of the nonpolar oil may include squalane (given by the formula 5), hydrogenated polydecene (given by the formula 6), etc.

[Formula 6]

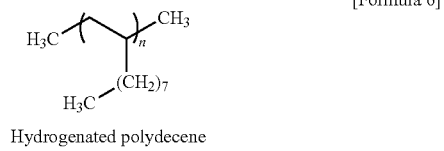

Hydrogenated polydecene

The gum as used herein may include at least one selected from the group consisting of xanthan gum, carrageenans gum, guar gum, gellan gum, and locust bean gum. The content of the gum may be in the range of 0.1 to 3 wt. % with respect to the total weight of the composition. The use of the gum enables to control the absorption rate of the composition by the skin, leaving the skin less greasy. The content of the gum greater than 3 wt. % causes the composition absorbed into skin before used by massage rolling, missing the timing for massage, which makes the composition useless as a cosmetic formulation for massage. The content of the gum less than 0.1 wt. % renders the composition not penetrating into skin.

As described above, the composition of the present invention contains 1 to 5 wt. % of a saccharide surfactant; 5 to 25 wt. % of an oil consisting of a polar oil and a nonpolar oil; and 0.1 to 3 wt. % of a gum, where the mixing ratio of the polar oil to the nonpolar oil is controlled in the range of 1~3:1, so that it enables to control the rolling sensation and the spreadability and provide a smooth massage control even with a low oil content relative to the conventional massage formulations, eliminates greasiness caused by high oil content, and easily penetrates into the skin by control of the absorption rate due to the use of gum, avoiding an inconvenience of cleansing the skin after use.

The composition of the present invention may be formulated into, if not specifically limited to, lotion, essence, cream, facial mask, or the like that belong to cosmetic products.

Hereinafter, the present invention will be described in further detail with reference to the following examples and comparative examples, which are not intended to limit the scope of the present invention.

REFERENCE EXAMPLE

Preparation of Cosmetic Composition for Massage

The essence-type emulsions in Examples 1, 2 and 3 of the present invention and Comparative Examples 1 to 6 were prepared according to the compositions given in the following Tables 1 and 2.

The oil phase consisting of ingredients 1 to 11 was put in a separate container, heated at 70° C. until melted, and then dispersed with a homogenizing unit to prepare a lipophilic mixture. As for the water phase (ingredients 12, 13 and 14), ingredients 13 and 14 were mixed together and then added to a purified water (ingredient 12). Once uniformly dispersed, the water phase was melted by heat at 75° C. to cause hydration, and then blended with the lipophilic mixture. The resultant mixture was emulsified into an oil-in-water emulsion with the homogenizing unit at 70° C. for 4 to 5 minutes. To the oil-in-water emulsion were added a thickener and an adequate amount of fragrance. The resultant mixture was agitated with the homogenizing unit for 3 minutes. Removed of bubbles with a degassing unit, the emulsion was poured into an airtight container and cooled down to the room temperature with a cooling unit.

TABLE 1

Ingredients and Content (wt. %) of Each Composition

| | | Example | | |
|---|---|---|---|---|
| No | Ingredient | 1 | 2 | 3 |
| 1 | Cetearyl alcohol | 0.4 | 0.4 | 0.4 |
| 2 | Glyceryl stearate | 1 | 1 | 1 |
| 3 | Stearic acid | 1 | 1 | 1 |
| 4 | C14-22 alcohol/C12-20 alkyl glucoside | 2 | 2 | 2 |
| 5 | Polysorbate 60 | 0 | 0 | 0 |
| 6 | Glyceryl stearate/PEG-100 stearate | 0 | 0 | 0 |
| 7 | Di-C12-13 alkyl malate | 5 | 3 | 7 |
| 8 | Cetyl ethyl hexanoate | 5 | 3 | 7 |
| 9 | Squalane | 3 | 1.5 | 4 |
| 10 | Hydrogenated polycedene | 2 | 1.5 | 3 |
| 11 | Dimethicone | 1 | 1 | 1 |
| 12 | Purified water | To 100 | To 100 | To 100 |
| 13 | Glycerin (Concentrated glycerin) | 7 | 7 | 7 |
| 14 | Xanthan gum | 0.5 | 0.5 | 0.5 |
| 15 | Thickener, Neutralizer | Adequate | | |
| 16 | Preservative, fragrance | Adequate | | |

TABLE 2

Ingredients and Content (wt. %) of Each Composition

| | | Comparative Example | | | | | |
|---|---|---|---|---|---|---|---|
| No | Ingredient | 1 | 2 | 3 | 4 | 5 | 6 |
| 1 | Cetearyl alcohol | 0.4 | 0.4 | 0.4 | 0.4 | 0.4 | 0.4 |
| 2 | Glyceryl stearate | 1 | 1 | 1 | 1 | 1 | 1 |
| 3 | Stearic acid | 1 | 1 | 1 | 1 | 1 | 1 |
| 4 | C14-22 alcohol/C12-20 alkyl glucoside | 0 | 2 | 2 | 2 | 2 | 2 |
| 5 | Polysorbate 60 | 1.5 | 0 | 0 | 0 | 0 | 0 |
| 6 | Glyceryl stearate/PEG-100 stearate | 0.5 | 0 | 0 | 0 | 0 | 0 |
| 7 | Di-C12-13 alkyl malate | 5 | 3.6 | 5.7 | 1.4 | 8.7 | 5 |
| 8 | Cetyl ethyl hexanoate | 5 | 3.6 | 5.7 | 1.4 | 8.7 | 5 |
| 9 | Squalane | 3 | 3.9 | 1.8 | 0.7 | 4.4 | 3 |
| 10 | Hydrogenated polycedene | 2 | 3.9 | 1.8 | 0.7 | 4.3 | 2 |
| 11 | Dimethicone | 1 | 1 | 1 | 1 | 1 | 1 |
| 12 | Purified water | To 100 | To 100 | To 100 | To 100 | To 100 | To 100 |
| 13 | Glycerin (Concentrated glycerin) | 7 | 7 | 7 | 7 | 7 | 7 |
| 14 | Xanthan gum | 0.5 | 0.5 | 0.5 | 0.5 | 0.5 | 0 |
| 15 | Thickener, Neutralizer | Adequate | | | | | |
| 16 | Preservative, fragrance | Adequate | | | | | |

EXPERIMENTAL EXAMPLE 1

Massage Control, Greasiness and Formulation Stability According to Surfactant Type and Oil Proportion The compositions of Example 1 and Comparative Examples 1, 2 and 3 were subjected to sensory evaluation in regard to massage control and greasiness. Each of twenty women panelists in their thirties answered to a survey for evaluation of the compositions in regard to massage control, with the composition of Example 1 applied on the one cheek, the compositions of Comparative Examples 1, 2 and 3 on the other. The massage control was evaluated based on the rolling sensation. As for the rolling sensation and the greasiness, the panelists scored the compositions of Comparative Examples 1, 2 and 3 from 0 to 20 points with reference to 10 points given to the composition of Example 1. The scores were averaged for each composition. As for the formulation stability, the compositions were kept at a constant temperature of 45° C. and evaluated based on the phase separation time. The results are shown in Table 3 and FIG. 1.

TABLE 3

| Experimental Example | Rolling Sensation (Massage Control) | Greasiness | Formulation Stability At 45° C. |
|---|---|---|---|
| Example 1 | 10 | 10 | Stable for 8 weeks |
| Comparative Example 1 | 5.1 | 9.8 | Stable for 8 weeks |
| Comparative Example 2 | 4.2 | 14.2 | Stable for 12 weeks |
| Comparative Example 3 | 14.6 | 6.8 | Stable for 4 weeks |

As can be seen from Table 3 and FIG. 1, the composition of Example 1 using a saccharide surfactant had a good massage control based on rolling sensation about twice as high as the composition of Comparative Example 1 using a PEG-based surfactant. Compared with the composition of Example 1 having a ratio of polar to nonpolar oils of 2:1, the composition of Comparative Example 2 having a ratio of polar to nonpolar oils of 0.923:1 (where the proportion of the polar oil was less than 1) showed a reduced massage control 0.42 times lower, with greasiness 1.46 times greater as the content of the nonpolar oil increased; and the composition of Comparative Example 3 having a ratio of polar to nonpolar oils of 3.16:1 (where the proportion of the polar oil was greater than 3) had an enhanced massage control 1.5 times greater, with a deterioration in the high-temperature formulation stability about 0.5 times lower.

EXPERIMENTAL EXAMPLE 2

Evaluation Test: Massage Control and Greasiness According to Oil Content and Presence of Gum The compositions of Examples 1, 2 and 3 and Comparative Examples 4, 5 and 6 were subjected to sensory evaluation in regard to massage control, absorption rate, and greasiness. Each of twenty women panelists in their thirties answered to a survey for evaluation of the compositions in regard to massage control, with the composition of Example 1 applied on the one cheek, the compositions of Examples 2 and 3 and Comparative Examples 4, 5 and 6 on the other. The massage control was evaluated based on the rolling sensation. The panelists scored the compositions of Examples 2 and 3 and Comparative Examples 4, 5 and 6 from 0 to 20 points with reference to 10 points given to the composition of Example 1. The scores were averaged for each composition. The results are shown in Table 4 and FIG. 2.

TABLE 4

| Experimental Example | Rolling Sensation (Massage Control) | Absorption Time | Greasiness | Need for Cleansing |
|---|---|---|---|---|
| Example 1 | 10 | 10 | 10 | 10 |
| Example 2 | 9.8 | 9.5 | 9.2 | 8.2 |
| Example 3 | 10.1 | 10.4 | 9.9 | 10.1 |
| Comparative Example 4 | 3.8 | 5.8 | 3.8 | 4.8 |
| Comparative Example 5 | 11.2 | 12.1 | 16.2 | 17.2 |
| Comparative Example 6 | 10.5 | 13.2 | 12.1 | 11.8 |

Figure 2:
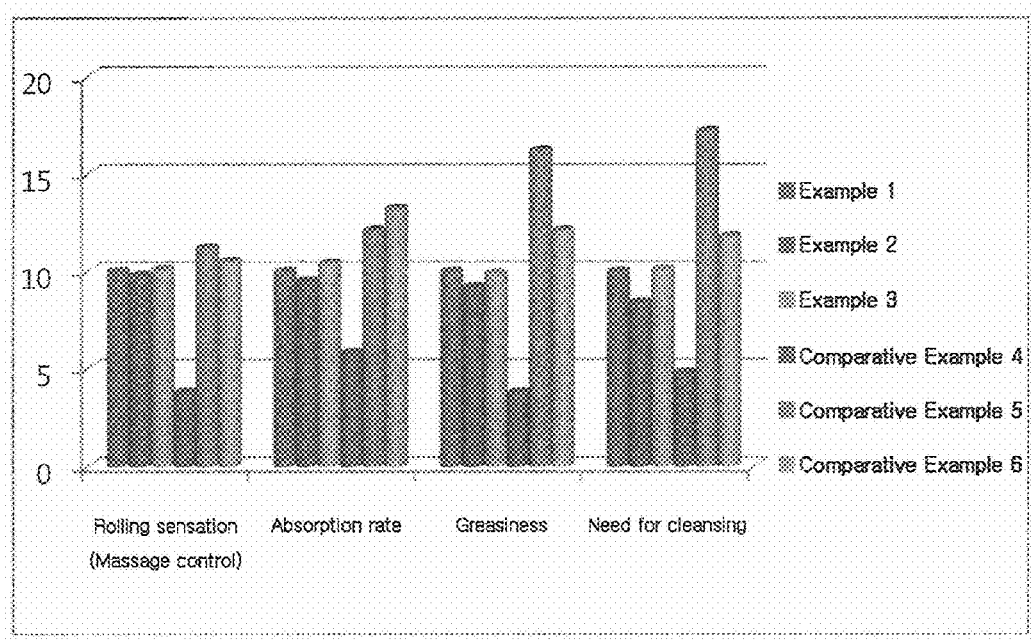
FIG. 2 shows the results of a sensory evaluation in regard to massage control, absorption rate, and greasiness as conducted on the compositions of Examples 1, 2 and 3 and Comparative Examples 4, 5 and 6.

As can be seen from Table 4 and FIG. 2, while the ratio of polar to nonpolar oils was constant as 2:1, the oil content was varied: 15 wt. %, 9 wt. %, and 21 wt. % for the compositions of Examples 1, 2 and 3, respectively; and 4.2 wt. % and 26.1 wt. % for the compositions of Comparative Examples 4 and 5, respectively. The compositions of Examples 1, 2 and 3 were almost equivalent to one another in the massage control. In spite of the oil content 1.7 times greater, the composition of Comparative Example 5 had an almost equivalent massage control about 1.1 times greater than the composition of Example 1. The results revealed that the massage control can be enhanced even with a low oil content less than 25 wt. % by controlling the ratio of polar to nonpolar oils in the range of 1~3:1.

On the other hand, the composition of Comparative Example 5 having a high oil content greater than 25 wt. % had an almost equivalent massage control about 1.1 times greater than the composition of Example 1 and a higher level of greasiness, with a need for cleansing 1.7 times greater, giving much more inconvenience after use.

When the oil content is less than 5 wt. %, as in the case of the composition of Comparative Example 4 containing 4.2 wt. % of oil, the massage control was greatly reduced to about 0.38 times the composition of Example 1. This showed that the composition is required to have at least 5 wt. % of oil.

As can be seen from Table 4, compared to the composition of Example 1 using a gum, the composition of Comparative Example 6 had a formulation absorption rate 13.2 times slower, higher greasiness, and an increased need of cleansing 1.28 times greater.

INDUSTRIAL APPLICABILITY

According to the experimental results, the present invention can provide an increased massage control even with a low oil content by a control of the oil ratio and control the absorption rate by using a gum, leaving the skin less greasy and avoiding an inconvenience of cleansing the skin after use.

The invention claimed is:
1. A cosmetic composition for massage comprising: with respect to the total weight of the composition,
  1 to 5 wt. % of a saccharide surfactant;
  5 to 25 wt. % of an oil, the oil comprising a polar oil and a nonpolar oil at a ratio of 2:1; and
  0.1 to 3 wt. % of a gum.
2. The cosmetic composition for massage as claimed in claim 1, wherein the saccharide surfactant is prepared from at least one saccharide selected from the group consisting of ribose, xylose, arabinoise, glucose, mannose, galactose, xylu- lose, and fructose by an esterification reaction with an alkyl fatty acid, or by an etherfication reaction with a cetearyl alcohol or a $C_{12-22}$ alcohol.

3. The cosmetic composition for massage as claimed in claim 1, wherein the polar oil comprises at least one functional group selected from the group consisting of carboxyl group (COO—), ketone group (CO—), and hydroxyl group (—OH).

4. The cosmetic composition for massage as claimed in claim 1, wherein the nonpolar oil is an hydrocarbon oil comprising hydrocarbon alone.

5. The cosmetic composition for massage as claimed in claim 1, wherein the gum comprises at least one selected from the group consisting of xanthan gum, carrageenans gum, guar gum, gellan gum, and locust bean gum.

6. A cosmetic composition for massage comprising, with respect to the total weight of the composition,
- 1 to 5 wt. % of a saccharide surfactant is prepared from at least one saccharide selected from the group consisting of ribose, xylose, arabinoise, glucose, mannose, galactose, xylulose, and fructose by an esterification reaction with an alkyl fatty acid, or by an etherfication reaction with a cetearyl alcohol or a $C_{12-22}$ alcohol;
- 5 to 25 wt. % of an oil, the oil comprising a polar oil having at least one functional group selected from the group consisting of carboxyl group (COO—), ketone group (CO—), and hydroxyl group (—OH) and a nonpolar hydrocarbon oil at a ratio of 2:1; and
- 0.1 to 3 wt. % of a gum comprising at least one gum selected from the group consisting of xanthan gum, carrageenans gum, guar gum, gellan gum, and locust bean gum.

* * * * *